United States Patent
Kropp et al.

(10) Patent No.: US 9,683,621 B2
(45) Date of Patent: Jun. 20, 2017

(54) ACTIVE ABSORBER FOR LOW-FREQUENCY VIBRATING STRUCTURES

(71) Applicant: Integrated Dynamics Engineering GmbH, Raunheim (DE)

(72) Inventors: Peter A. Kropp, Mainz (DE); Wolfram Sinn, Offenbach (DE)

(73) Assignee: INTEGRATED DYNAMICS ENGINEERING GMBH, Raunheim (DE)

( * ) Notice: Subject to any disclaimer, the term of this patent is extended or adjusted under 35 U.S.C. 154(b) by 398 days.

(21) Appl. No.: 13/971,360

(22) Filed: Aug. 20, 2013

(65) Prior Publication Data

US 2014/0093048 A1    Apr. 3, 2014

(30) Foreign Application Priority Data

Sep. 10, 2012  (EP) .................................... 12183680

(51) Int. Cl.
*F16F 7/10* (2006.01)
*B66C 13/06* (2006.01)
(Continued)

(52) U.S. Cl.
CPC .......... *F16F 7/1005* (2013.01); *B66C 13/066* (2013.01); *G01N 23/02* (2013.01); *G01V 5/0016* (2013.01)

(58) Field of Classification Search
CPC ..... B64C 27/001; B66C 13/22; B66C 13/066; B66C 15/00; G01N 23/02; F16F 7/002;
(Continued)

(56) References Cited

U.S. PATENT DOCUMENTS 5,111,697 A * 5/1992 Habermann ........... H02K 33/00
                                                              310/51
5,579,246 A * 11/1996 Ebersbach ........... G01B 21/045
                                                              33/503
(Continued)

FOREIGN PATENT DOCUMENTS

DE       19725770 A1    6/1997
DE       69414628 T2    6/1999
(Continued)

OTHER PUBLICATIONS

Machine Translation of EP2327651A1.*
(Continued)

*Primary Examiner* — Glen Kao
(74) *Attorney, Agent, or Firm* — Kaplan Breyer Schwarz, LLP

(57) ABSTRACT

An active vibration absorber is provided for damping vibrations of a cantilevered portion of a support structure. The vibration absorber comprises a mass, a drive and a control device. The mass is coupled without using a spring and through the drive to a fastening means for fastening the drive to the support structure, so that upon a movement of the mass relative to the fastening means an inertial force caused by this movement is directly transmitted through the drive to the fastening means. The control device comprising a motion sensor is adapted to control the drive in function of a signal from the motion sensor. The active vibration absorber is designed to damp especially low-frequency vibrating structures including more than one mass-spring element so that the vibration amplitude thereof is significantly reduced.

14 Claims, 7 Drawing Sheets

(51) Int. Cl.
*G01N 23/02* (2006.01)
*G01V 5/00* (2006.01)

(58) Field of Classification Search
CPC .... F16F 7/02; F16F 7/10; F16F 7/1005; F16F 15/002; F16F 15/02; F16F 15/022; G01V 5/0008; G01V 5/0016
See application file for complete search history.

(56) References Cited

U.S. PATENT DOCUMENTS

| | | | | |
|---|---|---|---|---|
| 5,627,440 | A * | 5/1997 | Yamamoto | G05B 19/416 318/568.21 |
| 5,638,304 | A * | 6/1997 | Billoud | F16F 15/002 702/56 |
| 5,666,770 | A | 9/1997 | Sato et al. | |
| 5,913,955 | A * | 6/1999 | Redmond | B23B 29/022 408/143 |
| 6,058,158 | A * | 5/2000 | Eiler | B66C 19/007 378/197 |
| 2003/0159508 | A1 | 8/2003 | Halsmer | |
| 2009/0294234 | A1* | 12/2009 | Kashani | F16F 15/0275 188/379 |
| 2010/0057260 | A1* | 3/2010 | Fallahi | F16F 7/1005 700/280 |

FOREIGN PATENT DOCUMENTS

| | | | |
|---|---|---|---|
| DE | 102004004299 A1 | 8/2005 | |
| DE | 102006056757 A1 | 6/2008 | |
| DE | 2006053232 B4 | 6/2010 | |
| DE | EP 2327651 A1 * | 6/2011 | ............ B66C 13/22 |
| DE | 102010002262 A1 | 8/2011 | |
| DE | 102010039977 A1 | 3/2012 | |
| EP | 0391130 A1 | 10/1990 | |
| EP | 0612058 A1 | 8/1994 | |
| EP | 0805288 A2 | 11/1997 | |
| EP | 618380 B1 | 11/1998 | |
| EP | 2327651 A1 | 6/2011 | |
| JP | 60155030 A | 8/1985 | |
| JP | S60155030 A | 8/1985 | |
| JP | H0658013 A | 3/1994 | |
| JP | H06503042 A | 4/1994 | |
| JP | H07-293038 | 7/1995 | |
| JP | H09134876 A | 5/1997 | |
| JP | H10133746 A | 5/1998 | |
| JP | H10259851 A | 9/1998 | |
| JP | H1151881 A | 2/1999 | |
| JP | H11194103 A | 7/1999 | |
| JP | H10055208 A | 9/1999 | |
| JP | 2002061703 A | 2/2002 | |
| JP | 2004100953 A | 4/2004 | |
| JP | 2004001597 A | 1/2008 | |
| JP | 2010078075 A | 4/2010 | |
| JP | 2010230310 A | 10/2010 | |
| JP | 2005211660 A | 8/2011 | |
| WO | 9220482 A1 | 11/1992 | |
| WO | 9953217 A1 | 10/1999 | |
| WO | 2008145122 A1 | 12/2008 | |

OTHER PUBLICATIONS

"Related European Patent Application No. EP 12 18 3680", "Office Action", Dec. 18, 2014, Publisher: EPO, Published in: EP.
"Related European Patent Application No. EP 12 18 3680 Partial Search Report", May 7, 2013, Publisher: EPO, Published in: EP.
Japanese Patent Application No. 2013-187360 "Office Action", Jan. 29, 2016, Publisher: JPO, Published in: JP.
"Japanese Office Action", issued in counterpart JP patent application No. 2013-187360, dated Sep. 15, 2015.

* cited by examiner

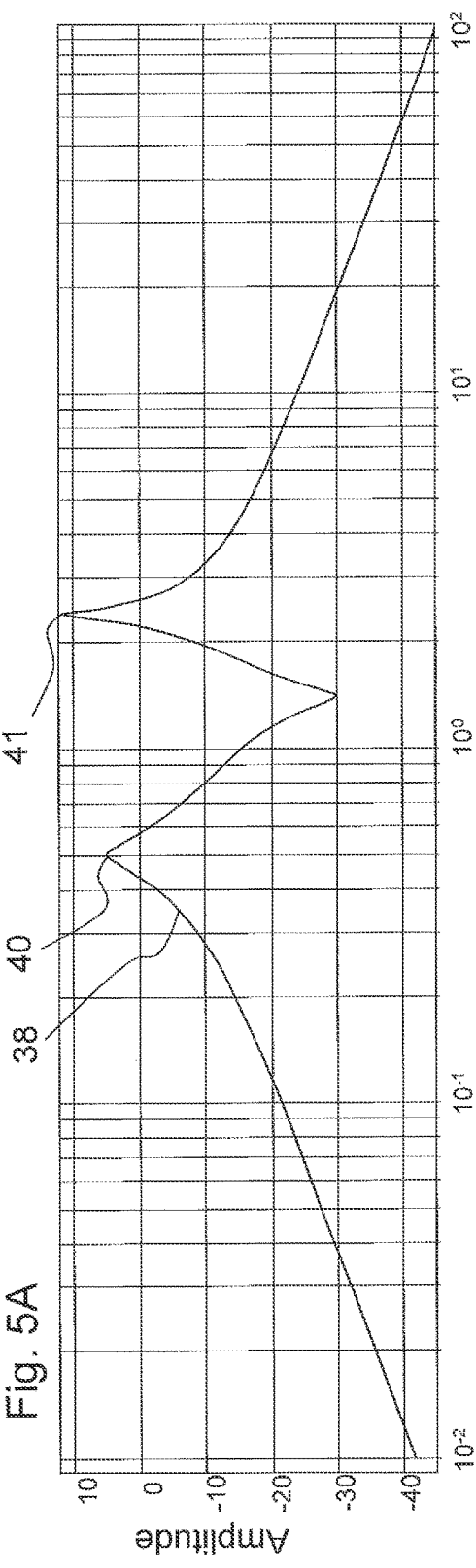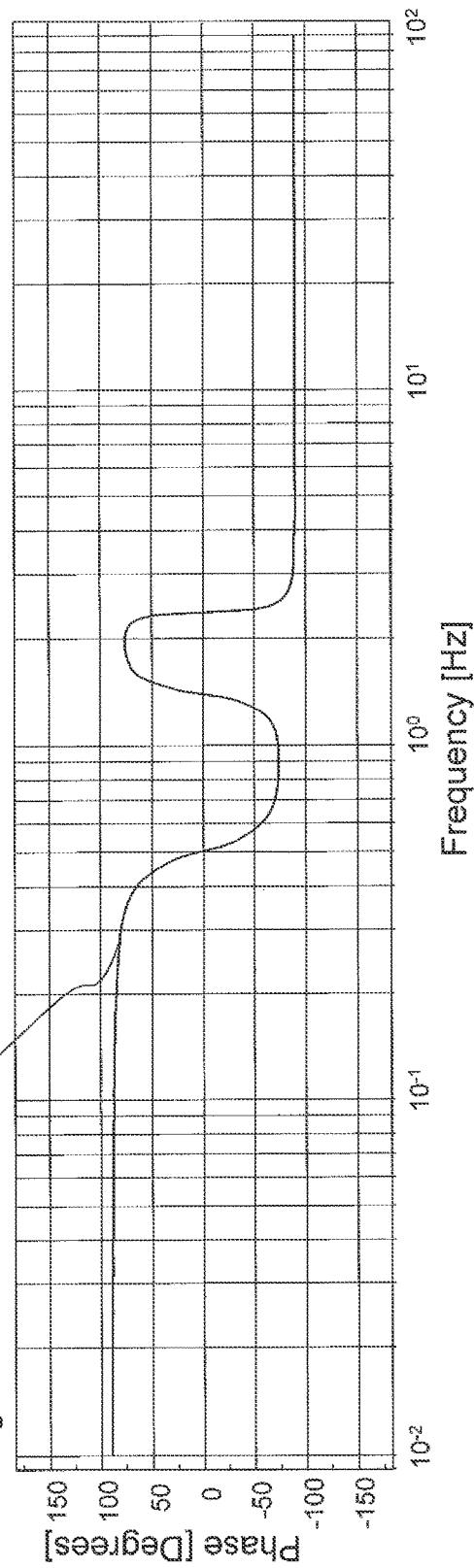
Fig. 5A
Fig. 5B

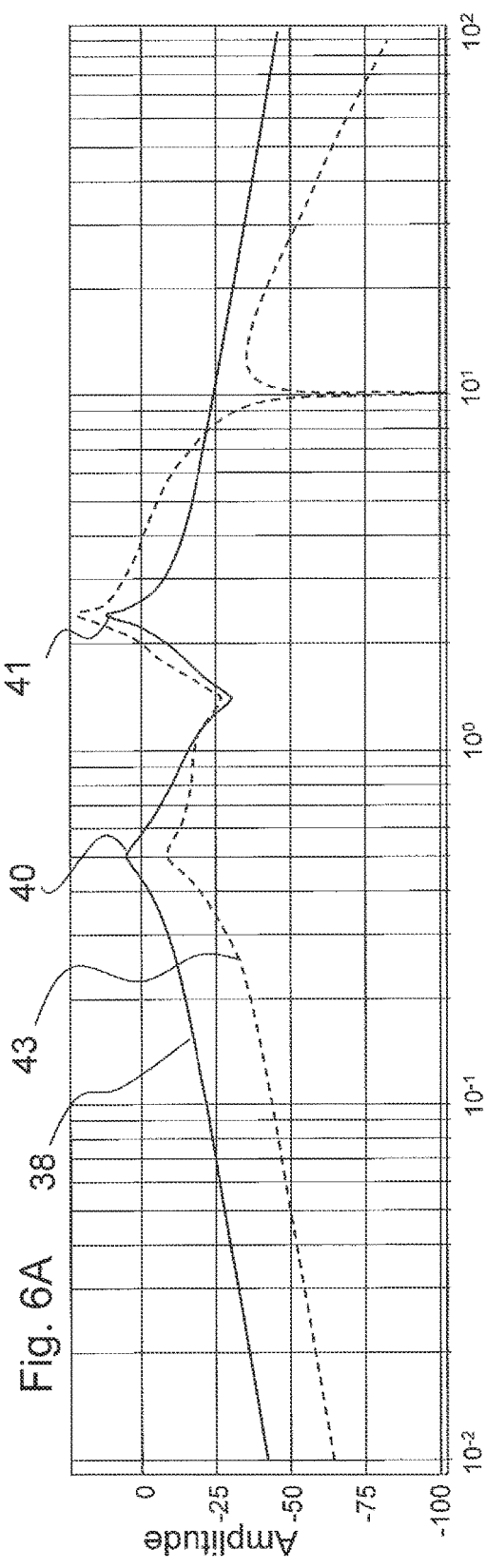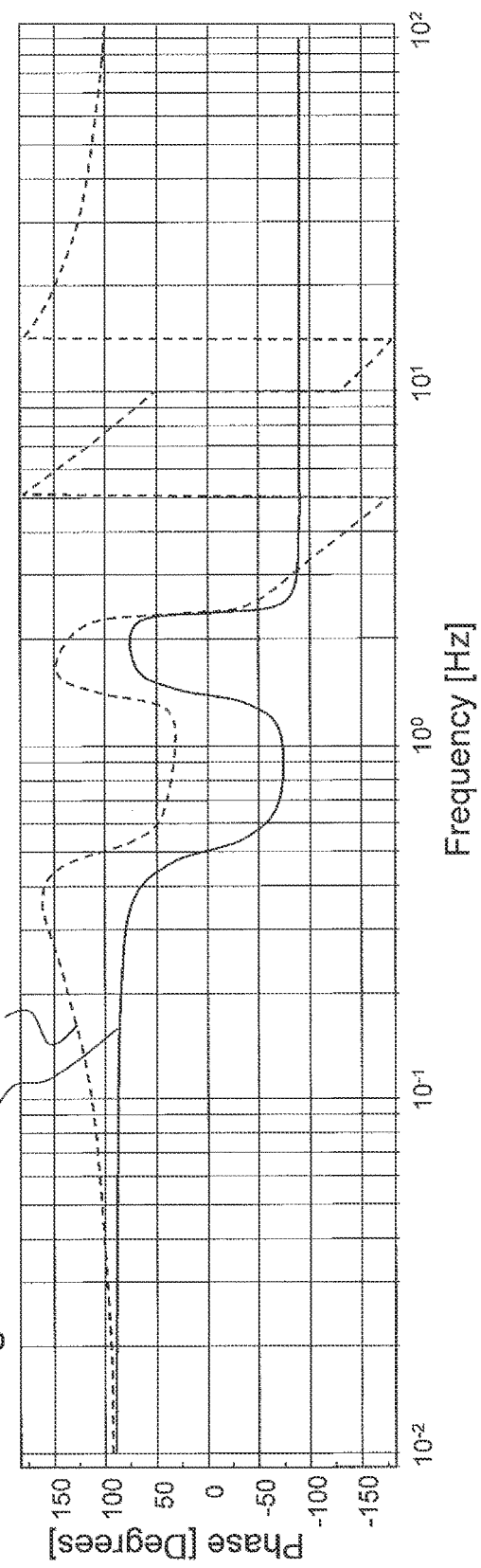

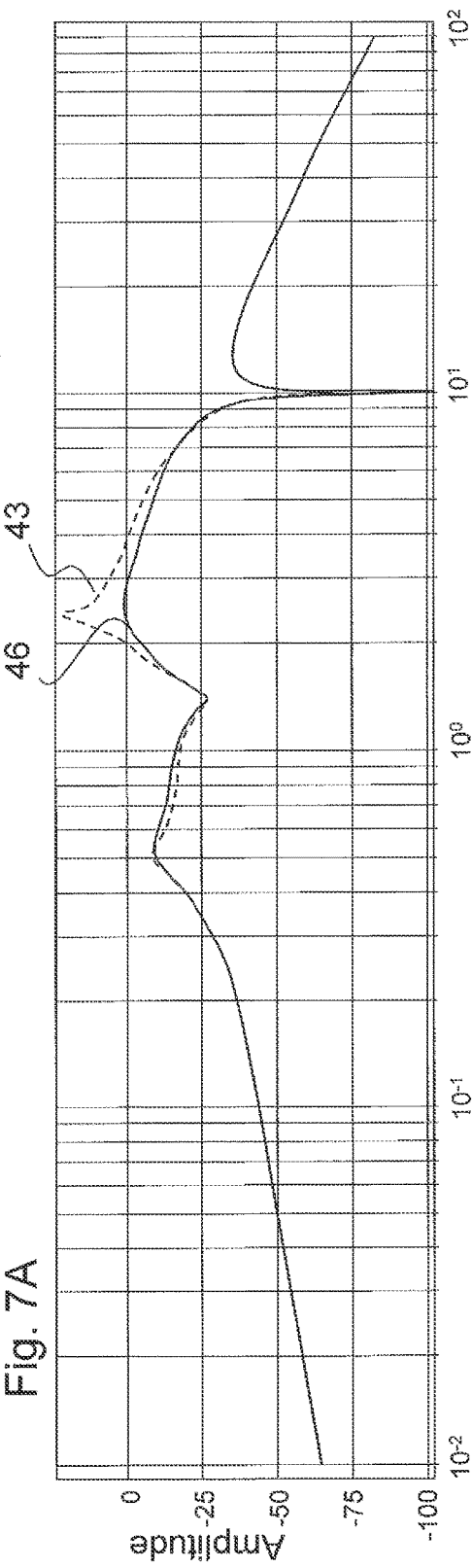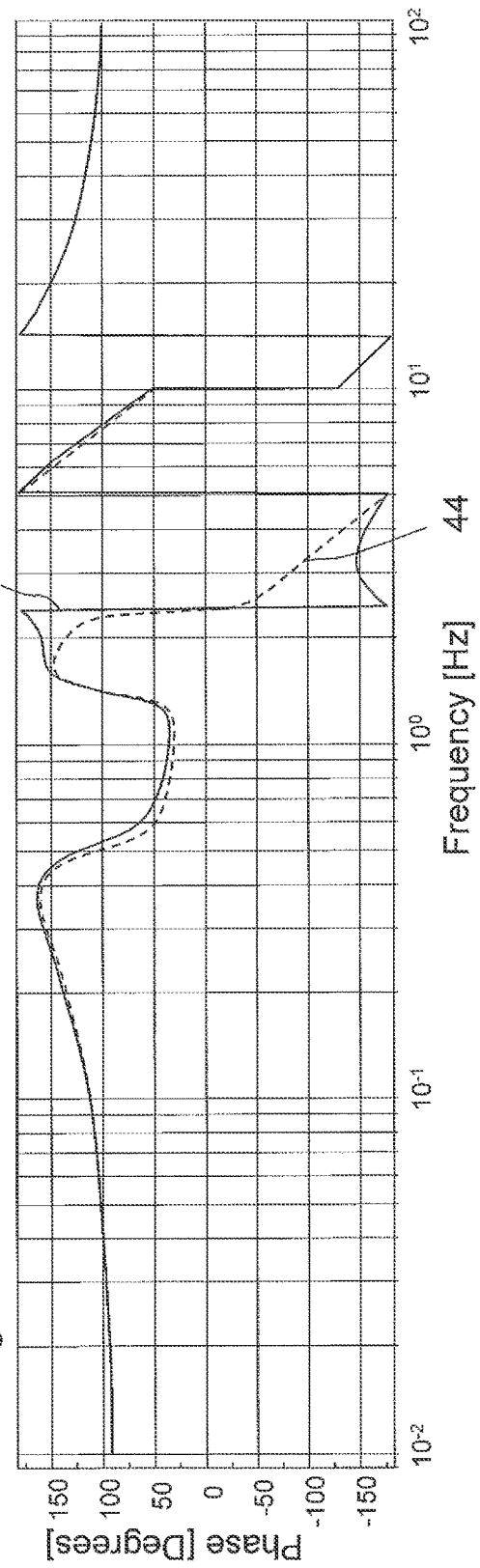

ACTIVE ABSORBER FOR LOW-FREQUENCY VIBRATING STRUCTURES

CROSS-REFERENCE TO RELATED APPLICATION(S)

European Patent Application No. EP 12 183 680.3, with a filing date of Sep. 10, 2012, is incorporated herein by reference.

FIELD OF THE INVENTION

The invention generally relates to vibration damping means. More particularly, the invention relates to an active vibration damping of a vibratory system using an absorber mass that is moved by a drive.

BACKGROUND OF THE INVENTION

Vibration damping means which are not attached between two portions but only to one vibrating portion of a device are referred to as a vibration absorber, or briefly as an absorber, or a pendulum-type absorber. Due to a stretchable or compressible connection between a mass of the absorber and the vibrating portion, the mass of the absorber follows the movements of the portion with a certain delay. Due to the stretching and/or compression, energy is withdrawn from the vibration movement, and in this way a damping effect is obtained.

Typically, the mass including the deformable connection, i.e. stretchable and/or compressible and/or twistable connection, has a natural frequency. The latter is usually set to a specific proportion of the vibration frequency to be damped. At this optimized frequency the mass will be deflected widely, so that correspondingly large forces and correspondingly large energies are transferred from the vibrating portion to the absorber mass.

From DE 197 25 770 A1 a device for damping vibrations is known which comprises a vibration absorber. The vibration absorber includes a mass resiliently coupled to the resilient system, the mass being coupled to the resilient system through a controllable actuator which is variable in length in the operating direction of the vibration absorber. This is intended to dampen vibrations in an enlarged frequency range as compared to a passive vibration damping system. Similar principles are also disclosed in DE 10 2006 056 757 A1 and DE 10 2010 002 262 A1, for damping vibrations of buildings.

The absorbers described in DE 6 941 4628 T2 and in EP 6 183 80 B1 are based on another mechanism of action. Here, the absorbers are attached to pendulum-like structures and virtually constitute a pendulum-type absorber. Specifically, a vibration absorber for cable car gondolas is provided, with a movable damping mass member attached to the pendulum structure of the gondola above the center of gravity thereof. EP 6 183 80 B1 furthermore gives an overview of industrial applications of absorbers which are likewise considered for the invention.

DE 10 2006 053 232 B4 discloses an absorber with two directions of action. This absorber is intended to damp a vibration of a conduit, for example, and may also be operated actively. The active absorber comprises at least two actuators acting in different movement directions, and a fastening device. The actuators are coupled to the fastening device via leaf springs. Additionally, the two actuators are coupled with each other by a connecting member.

DE 10 2010 039 977 A1 discloses a piston-shaped passive absorber which retains a balancing mass within a piston so as to be movable at a defined friction.

SUMMARY OF THE INVENTION

The invention aims to provide for dampening in particular low-frequency vibrating structures which include more than one mass-spring element or which exhibit vibration characteristics that can be described by a plurality of coupled mass-spring elements, in a manner so that the vibration amplitude thereof is significantly reduced. One application field of the invention are mobile or stationary X-ray scanners, for example.

For this purpose, an active vibration absorber is provided for damping vibrations of a cantilevered portion of a support structure, wherein the vibration absorber comprises a mass which is coupled to a fastening means without using a spring and typically mechanically, through a drive that is controlled by a control device of the vibration absorber, which fastening means serves to fasten the drive to a support structure to be damped, so that upon a movement of the mass relative to the fastening means an inertial force caused by this movement is directly transmitted via the drive to the fastening means. The control device comprises a motion sensor, the control device being adapted to control the drive in function of the signals from the motion sensor and thereby to dampen the vibrations of the support structure.

In other words, on the one hand the absorber mass is coupled to a first portion of the drive without using a spring, or rigidly, on the other hand a second portion of the drive, which is movable relative to the first portion, is coupled to the fastening means without using a spring, so that the only degree of freedom that remains for the movement of the absorber mass relative to the support structure to be damped and/or to the fastening means is a movement of the drive.

Accordingly, the invention also provides a support structure with active absorption, the support structure being retained at least at one end and having a cantilevered portion to which a vibration absorber is attached, in particular a vibration absorber as described above, wherein the vibration absorber comprises at least one mass which is movably mounted to be moveable at least along one direction by means of at least one drive, wherein the mass is coupled to the cantilevered portion of the support structure through the drive, so that upon a movement of the mass the drive directly exerts a force to the portion of the support structure, without interposition of a spring member.

Accordingly, the absorber forces are not generated by a combination of damping and inertia, but only by an acceleration of the absorber mass which is actively controlled by a control loop in a manner so that the movement detected by the motion sensor is damped by opposing forces.

So a direct, rigid connection via the drive is established herein with the system to be controlled, such as an arm having a cantilevered end, without using a common absorber spring. This eliminates the adaption of spring stiffness with respect to the vibratory system to be controlled. The inertia forces generated by the movement of the absorber mass are therefore directly transferred via the drive to the support structure to be damped. Similar to a swing where simultaneous swinging of one's legs leads to a strengthening of the rocking motion, a swinging of one's legs and body in the opposite direction would cause the rocking motion to come to a halt. This principle is also exploited by the invention, which enables to dampen a plurality of vibrational modes of different frequency.

It will be apparent to a person skilled in the art, how a spring-free coupling can be established between the absorber mass and the support structure to be damped via the drive. Although a rigid connection may also have associated therewith a spring constant, the latter will be much higher for the coupling of the absorbing mass than the spring constants of the support structure to be damped.

Accordingly, the lowest frequency of the natural vibration of the system of absorber mass and coupling thereof will be much higher. Generally, for the purposes of the invention, the spring-less coupling may be designed such that the lowest natural vibration mode of the system of absorber mass and coupling with the support structure or with the fastening means is at least four times, preferably at least eight times as high as the lowest frequency of the natural vibration of the support structure. The invention is in particular intended for damping low-frequency vibrations. Therefore, the coupling of the absorber mass through the drive to the fastening means for achieving a spring-less connection preferably has a significantly higher frequency of the lowest frequency natural vibration mode, which is preferably at least 10 Hz, more preferably at least 20 Hz.

Preferred motion sensors are velocity sensors, such as a geophone. However, an acceleration sensor is likewise conceivable as a motion sensor. A geophone is particularly suitable because it exhibits a high signal-to-noise ratio at low frequencies.

The absorber according to the invention is in particular intended to be mounted to a vibratory system with multiple degrees of freedom, which will be referred to as an "arm" below, for the sake of simplification and by way of example, in order to dampen the entire system in its vibrations. The absorber preferably comprises a linear drive as a drive which enables to move the mass in an axial direction, and a housing, and a fastening means by which the damper can be mounted to the end of the arm. The motion sensor, preferably a velocity sensor, is arranged at one of the non-movable parts of the absorber and is capable of sensing the movements of the arm's end and to supply it to a control loop of the control device.

This control loop will then supply a control signal to the linear drive in a manner so that the resulting movement (or acceleration which results in the movement) exerts a counter force on the system so that the overall movement of the arm is minimized.

BRIEF DESCRIPTION OF THE DRAWINGS

The invention will now be described in more detail by exemplary embodiments and with reference to the accompanying drawings. In the drawings, the same reference numerals refer to the same or to equivalent elements. In the drawings:

FIG. 5A shows the amplitude of the transfer function of a two-mass oscillator;

FIG. 5B shows the associated phase of the transfer function of the two-mass oscillator;

FIGS. 6A and 6B again show the amplitude (FIG. 6A) and phase (FIG. 6B) of the transfer function as illustrated in FIGS. 5A, 5B, and the respective amplitude and phase as controlled by a first control loop;

FIGS. 7A and 7B show the amplitude and phase of the transfer function as additionally controlled by a second control loop;

DETAILED DESCRIPTION

Figure 1:
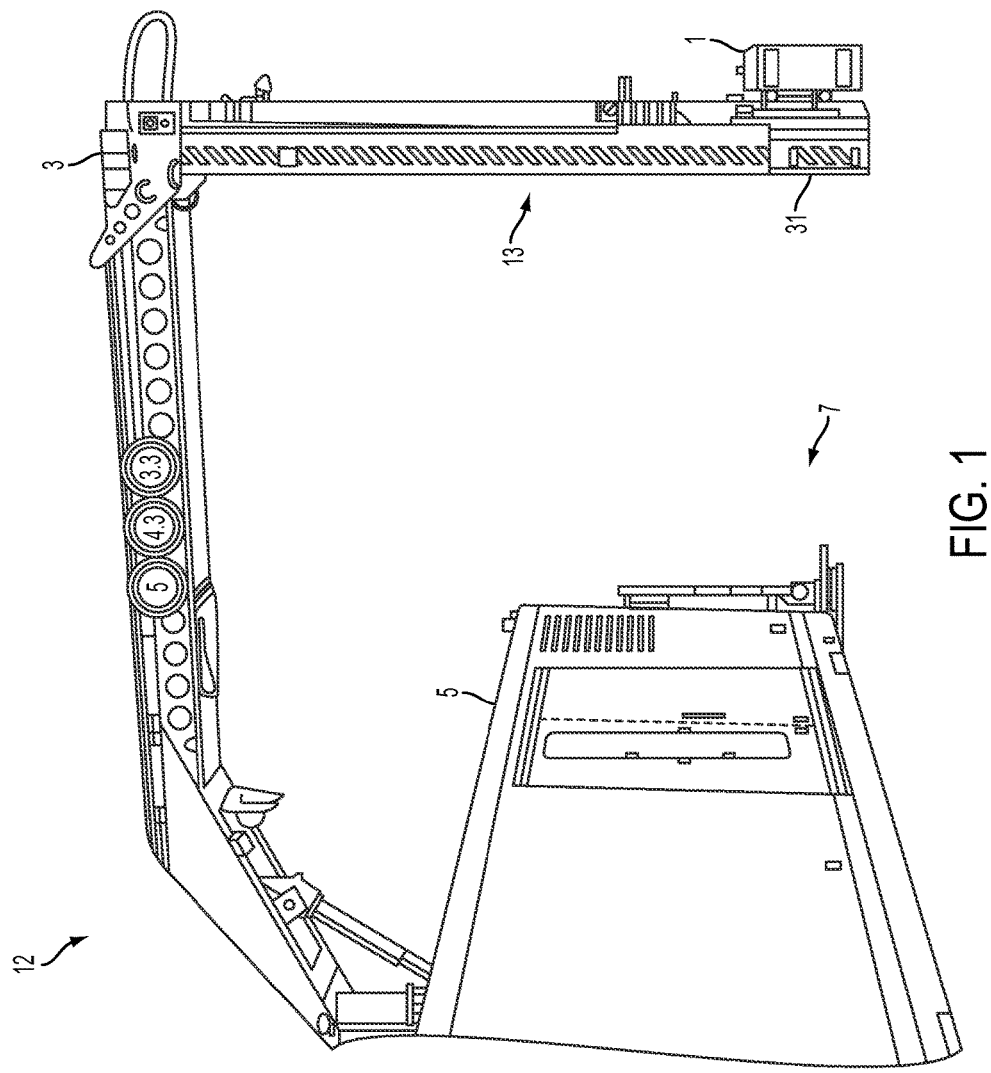
FIG. 1 is a view of one exemplary embodiment of a vibratory system in form of an X-ray scanner including an active absorber.

One embodiment of a vibratory system which represents one of the application cases thereof is shown in FIG. 1. This system is an X-ray scanner 12 for screening trucks or containers.

The X-ray scanner 12 of this exemplary embodiment comprises a container 5 which houses the measuring equipment for an X-ray scan. An arm 3 is mounted to container 5, and X-ray detectors 13 are attached to the arm. Detectors 13 are arranged at the side of arm 3 which faces the container, and therefore are hidden by the arm in the view of FIG. 1. In the example shown in FIG. 1, the detectors 13 are distributed along the vertical portion of arm 3 in order to detect a vertically fanned fan beam produced by the X-ray generator.

An active absorber 1 according to the invention is rigidly mounted by a fastening means, not shown, to the free or non-retained end 31 of arm 3. For a mobile use of this application, the container 5 may be placed onto a trailer of a semitrailer truck. This permits X-ray scanning of a stationary object, such as a truck with cargo, by driving therealong, while the truck or more generally the object to be checked passes through the intermediate space 7 between the container 5 and the end 31 of arm 3. In contrast to stationary installations where the cabin has generally to be occupied because the truck drives through the stationary X-ray scanner and therefore the truck cabin must not be scanned, mobile X-ray scanners may also check the cabin, because the latter does not have to be occupied.

While being moved by the semitrailer truck, the arm 3 is subjected to excitation at its base due to unevenness of the ground. This causes movements of the container 5 and hence of the arm 3. The vibrations of the arm 3 in turn may become so strong that the X-ray detectors at the inner side thereof will swing out of the X-ray path from the measurement container 5 and so will not produce any picture.

Therefore, without being limited to the example shown in FIG. 1, the invention also provides an X-ray scanner 12 which comprises an arm 3 which is anchored at one end and which is equipped at the other, free or non-anchored end 31 with an X-ray detector 13 or an X-ray generator, and with an active vibration absorber 1 according to the invention being arranged at this free end 31.

Figure 2:
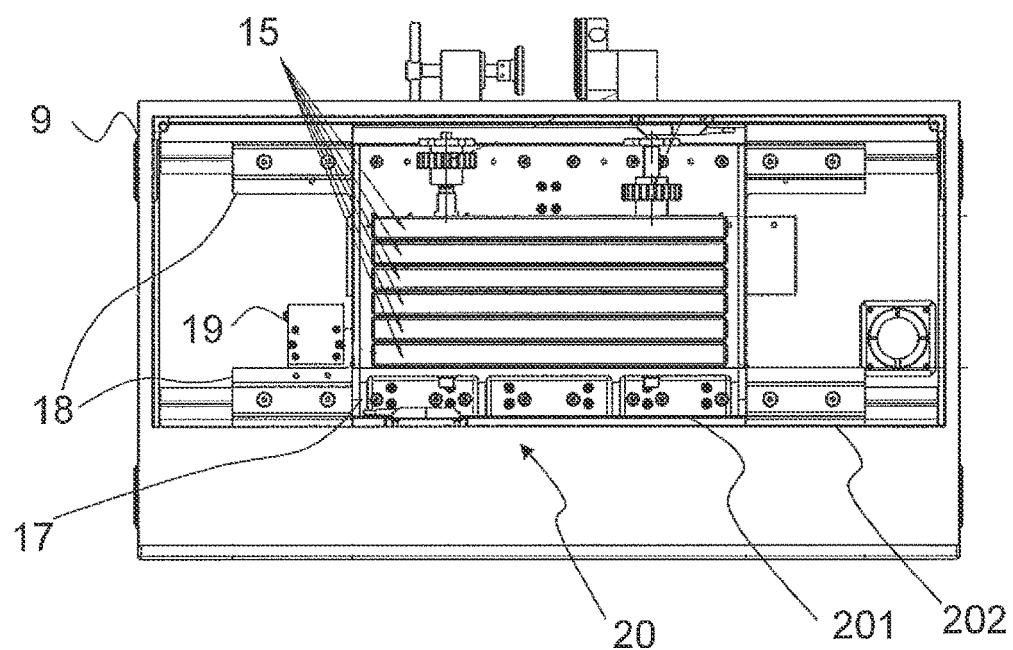
FIG. 2 is a view of the absorber with the housing opened.

FIG. 2 illustrates the absorber 1 with its housing 9 opened. A plurality of plate-shaped masses 15 can be seen there, which are mounted on a carriage 17 movable on rails 18. Carriage 17 also accommodates part of the drive 20 in form of a linear motor. Behind the carriage, the motion sensor 19 is disposed in the housing 9. Drive 20 comprises two parts 201, 202 that are movable relative to each other, the part 201 being connected to masses 15 without the use of a spring, and the part 202 being connected to the housing 9 without the use of a spring. Specifically, part 202 of the drive which is coupled to the housing 9 is formed by a rail on which the carriage 17 with the other part 201 of the linear motor is running.

As can be seen from FIGS. 1 and 2, the absorber 1 is attached to the outermost free end of arm 3. Here, two natural vibration modes can be measured simultaneously: a low frequency mode at which the entire arm is moved around its base, i.e. the retained or anchored end, and a higher frequency mode at which the vertical end portion of the arm swings around its upper suspension point.

Figure 3:
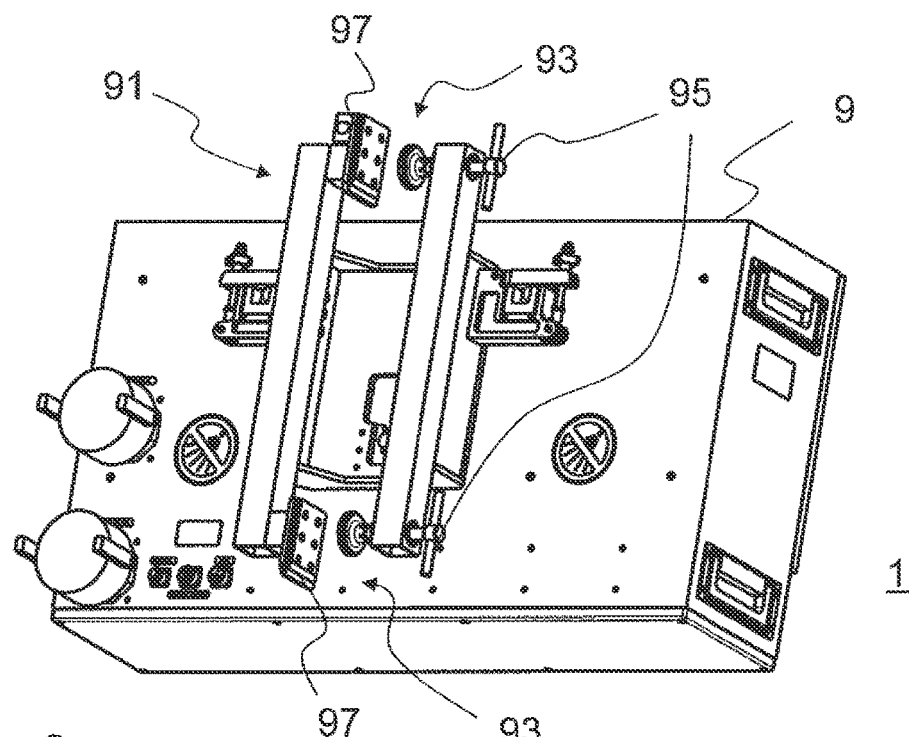
FIG. 3 is a view of the absorber housing from the opposite side.

FIG. 3 shows the housing 9 of absorber 1 from the opposite side. At this side, a fastening means 91 is arranged, by which the absorber 1 may be mounted to a support structure to be damped, that is at the end 31 of arm 3, for example.

Figure 4:
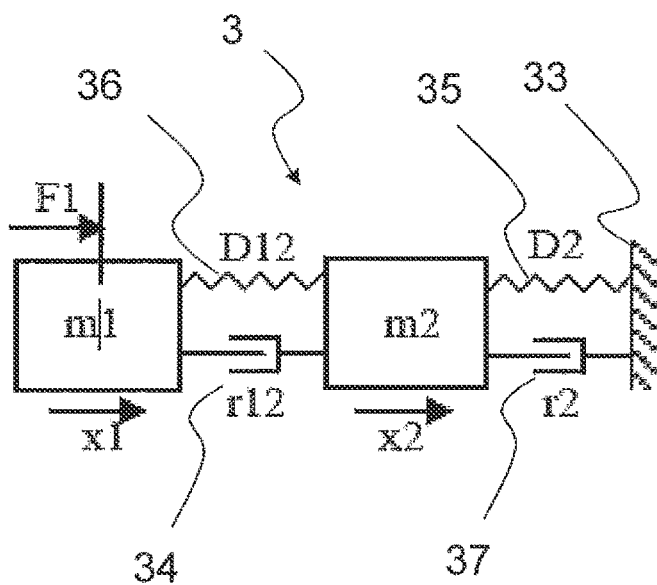
FIG. 4 is a schematic diagram of a spring-mass system.

FIG. 4 shows a schematic diagram of a spring-mass system. This spring-mass system is a model for describing the vibrations of a cantilevered arm, such as for example the arm of an X-ray scanner described with reference to FIGS. 1 and 2.

Such an arm 3 may be modeled, in terms of control technology, as a two-mass oscillator comprising masses m1 and m2, as illustrated in FIG. 4. Here, the mass m2 is attached at a fixed end 33 via a spring 35 having a spring constant D2. At the same time, the movement of mass m2 relative to the fixed end 33 is damped by an attenuator 37 having a damping constant r2.

Mass m2, in turn, has attached thereto a mass m1, via a spring 36 having a spring constant D12, the movement of masses m1, m2 relative to each other being damped by an attenuator 34 having a damping constant r12.

It can now be shown that by effecting control at the outer free end of the system, i.e. at m1 and accordingly at the end 31 in the example shown in FIG. 1, even the remote oscillator mass m2 can be controlled such that its movement is minimized, even if a force F1 only acts on m1.

Although according to the invention in this case the absorber is coupled to the arm without the use of an absorber spring, the equivalent system diagram of FIG. 4 reminds a standard absorber, with the spring constant D12 and damping r12 not being given by the absorber itself, but by the system (the arm 3).

However, the system cannot be compared with a standard absorber, because D12 and r12 are inaccessible to parameterization since they are system properties.

Rather, it is now largely the task of a control scheme to eliminate the mismatch of the natural frequencies in the sense of a standard absorber.

Useful for the invention herein are velocity feedback control techniques which have also been known for active vibration isolation systems. According to one embodiment of the invention, the sensor signal of a velocity meter such as a geophone which is proportional to the movement of m1, is looped back through a controller which is preferably implemented digitally and allows for control loops that are parameterizable in wide ranges.

This control signal may then be fed to an amplifier for the drive, i.e. a linear motor in the example shown in FIGS. 1, 2.

Depending on the configuration, the amplifier may use this signal as a target signal for a motor current or for a translational speed. The use directly as a motor current is advantageous, since the velocity of the arm is to be directly counteracted by a force. Since the current supplied to the linear motor is proportional to the acceleration thereof, this would be achieved immediately.

On the other hand, linear drives exhibit a non-linear characteristic for small amplitudes, which is caused by the breakaway torque of the mechanical components at the start of a movement. Therefore such a signal is not a reliable basis.

Instead, a phase shift of 90 degrees is accounted for and the control signal is intended to determine the target velocity. This allows an amplifier of the linear motor, or more generally of the drive, to take on the task to drive the current to a level, in every moment, so that the target speed is really achieved. A non-linearity is thus avoided.

Therefore, according to a further embodiment, the vibration absorber comprises an amplifier or a driver for providing the supply current for the drive, wherein the control device is adapted to supply a signal to the amplifier as an output signal which corresponds to the target velocity of the drive.

The so-called open-loop transfer function of a two-mass oscillator as shown above in FIG. 4 is illustrated in FIGS. 5A and 5B. FIG. 5A herein shows the magnitude or amplitude 38, and FIG. 5B shows the phase 39 of the transfer function.

First of all it can be seen that the amplitude of the transfer function has two maxima. The first peak 40 of the illustrated example is at a frequency of about 0.5 Hz, the second, higher frequency peak is at about 2.5 Hz. These maxima correspond to the vibration modes of arm 3 mentioned above. The maximum at 0.5 Hz is caused by the low frequency mode at which the entire arm swings around its base. The natural mode at 2.5 Hz corresponds to the oscillation of the vertical end portion of the arm around its upper suspension point.

As can be further seen from FIG. 5B, the phase curve exhibits a course unfavorable in terms of controlling, because at 0.5 Hz with a high amplitude it slowly crosses zero. It is therefore unfavorable to close the control loop by means of a simple P controller.

However, it has proven to be very effective to use two control loops or two controllers for control purposes. Specifically, according to one embodiment of the invention without any limitation to the specific exemplary embodiments described herein the control device comprises at least two control loops, the control loops being adapted to generate control signals for different vibration frequencies.

Specifically, in one embodiment of the invention the absorber according to the invention, which is only shown herein by way of example, employs two control loops with the same input signal from the motion sensor, such as preferably a geophone, and first controls the higher frequency portion in one control loop, then the lower frequency portion.

According to still another embodiment of the invention, for control purposes the open loop or controlling of a first control loop is adapted so that the amplitude at 0.5 Hz is lowered and the phase is appropriately shifted such that the frequency of this oscillation is not affected. FIGS. 6A and 6B show again the amplitude and phase of the exemplary embodiment of FIGS. 5A and 5B, and for comparison purposes also show the amplitude 43 and phase 44 as controlled by the first control loop. In the example shown, the controller of the first control loop suppresses frequencies around 10 Hz by means of a cascade filter, by way of example.

Finally, FIGS. 7A and 7B show the transfer functions for the amplitude (FIG. 7A, reference numeral 46) and phase (FIG. 7B, reference numeral 47) at the absorber as additionally controlled by a second control loop. The amplitude 43 and phase 44 as controlled by the first control loop of FIG. 6A, 6B are also shown, for comparison purposes.

Without being limited to the exemplary embodiment shown, the second control loop according to one embodiment of the invention comprises a band-pass. More generally, therefore, at least one of a plurality of control loops of the control device may comprise a band-pass.

As will be apparent from a comparison of FIGS. 5A and 7A, the second control loop permits to achieve a reduction of the oscillation amplitude of more than 20 dB in this way. In the exemplary embodiment illustrated in FIGS. 7A, 7B, the second control loop implemented as a band-pass or comprising a band-pass is parameterized in such a manner that it is effective in a frequency range that includes one of the vibration modes of the support structure, or the arm 3 in the present case. In the example shown in FIGS. 7A and 7B, this is the higher frequency mode, which in this case is at about 2.5 Hz.

In the two figures, this can be seen from the fact that in a range around this frequency the phase and amplitude are altered, whereas vibrations at more distant frequencies, such as above 10 Hz or below 0.2 Hz are not affected or controlled. Therefore, according to one embodiment of the invention, an inventive support structure is provided with an active absorber, in which the control device comprises at least two control loops which are adapted for controlling vibrations in different frequency ranges, wherein the support structure has at least two vibration modes, and wherein at least one of the control loops is implemented as a band-pass and effects control in a frequency range which includes one of the vibration modes.

The example shows that even with an unfavorable position of the frequencies and phases, the digital control loops which are adjustable over a wide range enable to always find a parameter set which effectively damps the movements.

It is generally advantageous for the absorber to be attached to a point of the support structure at which only one vibration mode occurs, for selectively damping only this one. Instead, a point is carefully chosen, at which at least two vibration modes or natural oscillations superimpose, such as the outer point of arm 3 in this case.

Furthermore, generally, the invention is especially suitable for damping low-frequency vibrations. Preferably, the absorber is adapted for damping vibrations below 50 Hz, preferably below 20 Hz, more preferably below 10 Hz. With respect to the plurality of vibration modes mentioned above this means that the vibration modes of the support structure are preferably in the aforementioned frequency ranges.

From the embodiments described above by way of example only it will also be apparent that in contrast to known vibration absorbers a parameter of the absorber will not be matched to a system only once, but preferably any excitation of the system will be prevented by means of a wideband feedback control loop. This enable to respond to disturbances induced by excitation at the base as well as to disturbances induced externally. Moreover, because of the active control it is superior in terms of respond time over any system operating through friction/damping loss.

Thus, the design of the active absorber according to the invention may be restricted to an adaptation of the movable mass 15, the necessary accelerations, and the travel distance of the absorber mass 15 to the respective vibratory system.

Figure 8:
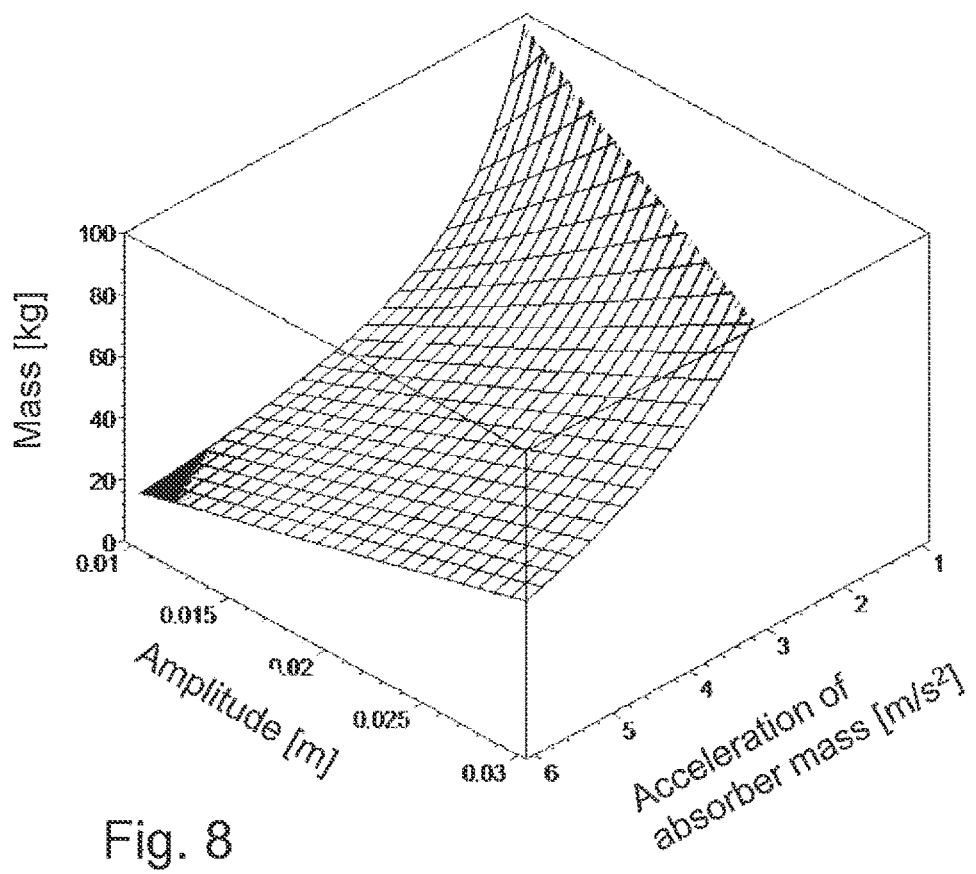
FIG. 8 shows a 3D plot of the relationship between the amplitude of oscillation of an arm having an active absorber attached thereto, the acceleration, and the mass of the absorber weight.

An example of parameter dependency of a vibratory support structure is illustrated by the 3D diagram of FIG. 8. The diagram of FIG. 8 shows the required accelerations of the absorber masses and the required mass of the absorber mass for expected amplitudes of arm movement. The functional relationship shown in FIG. 8 is easily derived using Newton's force law.

Figure 9:
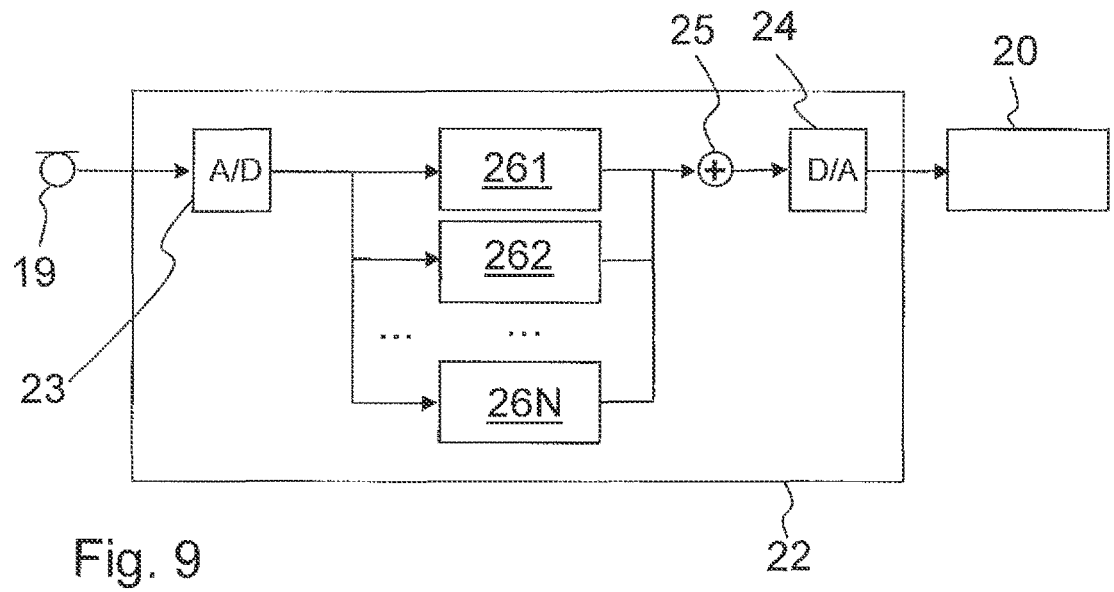
FIG. 9 shows a diagram of one exemplary embodiment of a control device.

FIG. 9 schematically shows an exemplary embodiment of a control device including a plurality of control loops. The principle of this control device 22 is based on the fact that the control device comprises at least two parallel controllers 261, 262, . . . , 26N, wherein each controller 261, 262, . . . , 26N receives the signal from a motion sensor 19 as an input signal, and wherein the control device 22 comprises an adder 25 which adds the output signals from controllers 261, 262, . . . , 26N.

Preferably a velocity sensor whose signal is proportional to the movement of the arm is used as a motion sensor for feedback control. The signal from this motion sensor is digitized by an analog-to-digital converter 23 of the control device 22, and is supplied in parallel to controllers 261, 262, . . . , 26N, which in turn may comprise cascade filters. According to one exemplary embodiment, up to 8 different cascade filters may be used on the same input signal. It has been found that for the application example of an arm 3 as shown in FIG. 1 the transfer function is advantageously processed using two parallel controllers 261, 262. According to one modification of the invention, one of the controllers 261, 262 comprises a cascade of a lead-lag filter and a PID filter. It goes without saying that such a cascade may also be useful for damping other types of vibratory support structures.

More generally, control device 22 may comprise any cascade of digital filters which may be selectable and/or parameterizable in the field.

According to one exemplary embodiment, the low-frequency mode (0.5 Hz) as shown in FIG. 5A is then combined in parallel with a controller cascade as a second controller 262, which is defined by a band-pass filtering at 0.5 Hz, a lead-lag, and a PID filter.

The individual output signals of the parallel configurations are digitally summed by an adder 25 and are supplied to a digital-to-analog converter 24 which provides the control signal for the actuator or drive 20.

Control device 22 is preferably implemented digitally, as is specifically the case in the example of FIG. 9. This enables the controllers to be adjusted to the vibration behavior of the respective support structure in a very freely parameterizable manner.

Also, the parallel connection of individual controllers 261, . . . , 26N as shown in FIG. 9 is particularly advantageous in conjunction with the invention, since in this way the controllers may be adjusted individually to the various superimposing vibrational modes occurring. In this manner, each of controllers 261, . . . , 26N may be adjusted individually to specific vibration modes. Since vibrations superimpose undisturbed, due to the parallel connection the control signals for the drive are superimposed in the same manner by the adder.

In the exemplary embodiment shown in FIGS. 1 and 2, an absorber mass is provided which may be moved substantially horizontally by means of drive 20, in order to avoid that due to vibrations of the arm 3 the X-ray detectors laterally move out of a fan beam generated by X-ray generators and fanned out in a vertical direction. It will be appreciated, however, that the invention may also be extended for damping vibrations in several different directions.

Figure 10:
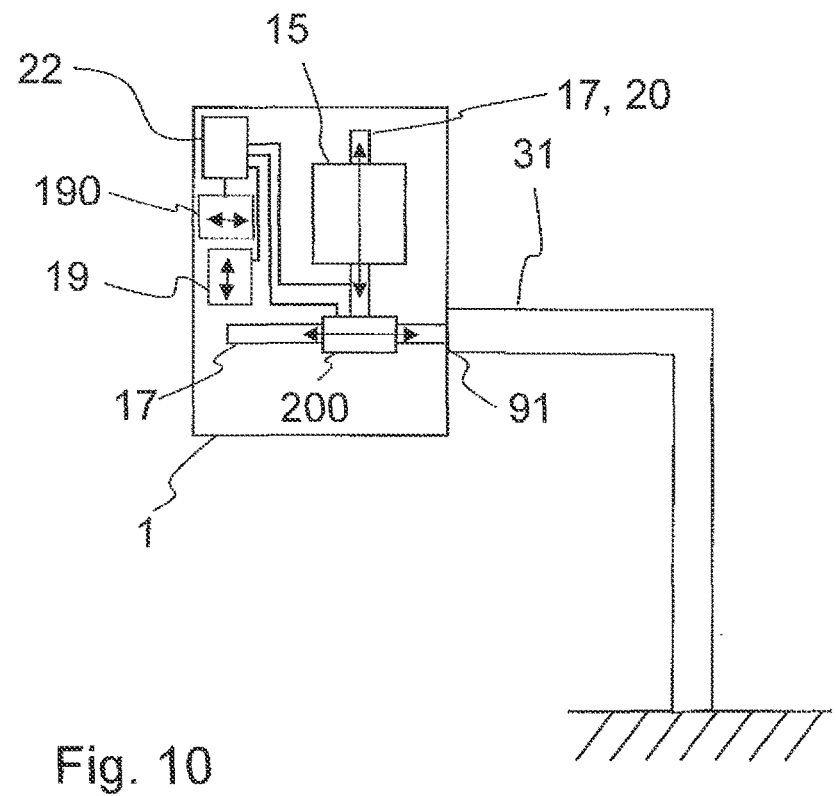
FIG. 10 shows one embodiment of the invention which includes a plurality of drives.

For example, FIG. 10 schematically shows another embodiment of the invention. Here, an absorber mass 15 is attached to an end of an arm 3 vibratory in two directions. Absorber 1 comprises two carriages 17 superposed to one another, each one equipped with its own drive 20, or 200. In this manner, drives 20, 200 will move the absorber mass 15 in different, preferably orthogonal directions. For each direction, a separate motion sensor 19, 190 is provided, whose signals are processed by control device 22. The direction of motion detection by sensors 19, 190 is marked by a respective double arrow. Accordingly, sensor 19 is associated with drive 20, and sensor 190 is associated with drive 200.

The processing and feedback control may be easily effected separately for each drive 20, 200 and the associated motion sensor 19, 190. Accordingly, two independently operating control devices 22 could be provided instead.

In the illustrated example, the vibrations are damped in a plurality of directions using a shared absorber mass 15. However, it is likewise possible to provide separate absorber masses 15. Furthermore, it is also possible for the input signals to be detected by a single motion sensor 19 which is sensitive in several spatial directions. The signals from such a motion sensor 19 may then be disassembled into components of individual spatial directions and may be processed separately by control device 22.

Therefore, for damping orthogonal vibration modes, one embodiment of the invention without any limitation to the example shown in FIG. 9 provides a support structure with active absorption, wherein the active absorber comprises at least two drives, by means of which one or more absorber masses 15 are movable in different, preferably orthogonal directions as controlled by the control device 22. Mutually perpendicular directions are advantageous in order to avoid crosstalk. If the directions are not perpendicular to each other, a movement of an absorber mass in one direction will also cause a force along the other direction. Preferably, the control device controls the movement of the one or more mass(es) 15 along the different directions independently from each other based on signals of movements along these directions, those signals being generated by one or more motion sensors 19, 190.

LIST OF REFERENCE NUMERALS

1 Active vibration absorber
3 Arm
5 Container
7 Intermediate space between 5, 31
9 Housing
12 X-ray scanner
13 X-ray detector
15 Mass
17 Carriage
18 Rail
19, 190 Motion sensor
20, 200 Drive
201, 202 Mutually movable parts of the drive
22 Control device
23 A/D converter
24 D/A converter
25 Adder
31 End of arm 3
33 Fixed end
35, 36 Spring
34, 37 Attenuator
38, 43, 46 Amplitude of transfer function
39, 44, 47 Phase of transfer function
40, 41 Maxima of transfer function
91 Fastening means
93 Screw clamp
95 Thumb screw
97 Abutment
261, 262, 26N Controllers

What is claimed is:

1. An active vibration absorber for damping vibrations of a cantilevered portion of a support structure, the vibration absorber comprising a mass, a linear drive and a control device,
   wherein said mass is coupled, without using a spring and through the drive, with a fastening means for fastening said drive to the support structure, so that upon a movement of the mass in an axial direction relative to the fastening means an inertial force caused by said movement is directly transmitted through the drive to the fastening means, and
   wherein the control device comprises a motion sensor sensing movements subjected to damping and at least two control loops with inputs that are electrically connected with the motion sensor, and
   wherein each of the control loops, of which at least one comprises a band-pass, is designed as a feedback controller that receives an input signal from said motion sensor, the control loops thus being adapted for controlling the drive to vibrate in different frequency ranges in function of the signal from said motion sensor.

2. The active vibration absorber as claimed in claim 1, wherein the control device has at least two parallel controllers, each controller receiving the signal from the motion sensor as an input signal, and wherein the control device comprises an adder for adding the output signals from the controllers.

3. The active vibration absorber as claimed in claim 1, wherein the motion sensor comprises a velocity sensor.

4. The active vibration absorber as claimed in claim 1, further comprising an amplifier for providing a supply current for the drive, wherein the control device is adapted to supply a signal corresponding to the target speed of the drive as an output signal to the amplifier.

5. The active vibration absorber as claimed in claim 1, wherein the drive comprises a linear motor.

6. The active vibration absorber as claimed in claim 1, wherein the vibration absorber is adapted for damping vibrations below 50 Hz.

7. The active vibration absorber as claimed in claim 6, wherein the vibration absorber is adapted for damping vibrations below 20 Hz.

8. The active vibration absorber as claimed in claim 7, wherein the vibration absorber is adapted for damping vibrations below 10 Hz.

9. An X-ray scanner (12), comprising an arm which is anchored at one end thereof and is provided with an X ray detector or an X-ray generator at the other, free end thereof, with an active vibration absorber as claimed in claim 1 being arranged at said free end.

10. A support structure with active absorption, wherein the support structure is secured at least at one end thereof and has a cantilevered portion, to which a vibration absorber is attached, wherein the vibration absorber includes at least one movably mounted mass which is movable at least along one direction by means of at least one drive, wherein the mass is coupled to the cantilevered portion of the support structure through the drive in such a manner that upon a movement of the mass the drive exerts a force, directly and without interposition of a spring member, to said portion of the support structure, wherein the vibration absorber includes a control device that comprises a motion sensor sensing movements subjected to damping and at least two control loops with inputs that are electrically connected with the motion sensor, wherein each of the control loops, of which at least one comprises a band-pass, is designed as a feedback controller that receives an input signal from said motion sensor, the control loops thus being adapted for controlling vibrations in different frequency ranges in function of the signal from said motion sensor.

11. The support structure as claimed in claim 10, wherein the support structure is formed as a cantilevered arm, the vibration absorber being disposed at the free end (31) of the arm.

12. The support structure as claimed in claim 11, wherein the support structure has at least two vibration modes, and wherein at least one of the control loops is implemented as a band-pass and adapted for controlling in a frequency range which includes one of said vibration modes.

13. The support structure with active absorption as claimed in claim 11, wherein the active absorber includes at least two drives, by means of which one or more absorber masses are movable in orthogonal directions as controlled by the control device.

14. The support structure as claimed in claim 10, wherein the vibration absorber is arranged at a point of the support structure at which a superposition of at least two vibration modes occurs.

* * * * *